United States Patent [19]
Fahrenkrug et al.

[11] Patent Number: 5,135,522
[45] Date of Patent: Aug. 4, 1992

[54] DIAPER HAVING DISPOSABLE CHASSIS ASSEMBLY AND REUSEABLE ELASTICIZED BELT REMOVABLY RETAINED BY SAID CHASSIS ASSEMBLY

[75] Inventors: Anne M. Fahrenkrug, Oshkosh; Patrick R. Lord, Neenah, both of Wis.

[73] Assignee: Kimberly-Clark Corporation, Neenah, Wis.

[21] Appl. No.: 790,103

[22] Filed: Nov. 7, 1991

Related U.S. Application Data

[63] Continuation of Ser. No. 504,159, Apr. 2, 1990, abandoned.

[51] Int. Cl.$^5$ .................... A61F 13/74; A61F 13/64
[52] U.S. Cl. .................... 604/385.1; 604/378; 604/385.2; 604/392; 604/401; 604/393
[58] Field of Search ............ 604/392, 401, 402, 385.1, 604/385.2, 393, 400, 378

[56] References Cited

U.S. PATENT DOCUMENTS

| | | | |
|---|---|---|---|
| D. 121,647 | 7/1940 | Coleman . | |
| D. 132,937 | 6/1942 | Cadgene . | |
| D. 290,780 | 7/1987 | Wistrand . | |
| D. 306,209 | 2/1990 | Coates et al. | D24/50 |
| 438,537 | 10/1890 | Fuller | 604/401 |
| 1,646,880 | 3/1925 | Schaffer | 604/402 |
| 2,141,105 | 12/1938 | Eller et al. | 128/284 |
| 2,509,674 | 5/1950 | Cohen | 128/284 |
| 2,516,951 | 8/1950 | Brink | 128/287 |
| 2,638,899 | 5/1953 | Ambarian | 604/401 X |
| 2,798,489 | 7/1957 | Behrman | 604/401 X |
| 3,196,874 | 7/1965 | Hrubecky | 128/287 |
| 3,227,160 | 1/1966 | Younger | 604/401 X |
| 3,370,590 | 2/1968 | Hokanson et al. | 128/290 |
| 3,635,221 | 1/1972 | Champaigne | 604/401 X |
| 3,653,381 | 4/1972 | Warnken | 128/284 |
| 3,658,064 | 4/1972 | Pociluyko | 128/287 |
| 4,050,462 | 9/1977 | Woon et al. | 128/287 |
| 4,182,334 | 1/1980 | Johnson | 604/402 X |
| 4,315,508 | 2/1982 | Bolick | 128/289 |
| 4,324,245 | 4/1982 | Mesek et al. | 128/287 |
| 4,397,645 | 8/1983 | Buell | 604/380 |
| 4,397,646 | 8/1983 | Daniels et al. | 604/381 |
| 4,425,128 | 1/1984 | Motomura | 604/381 |
| 4,496,360 | 1/1985 | Joffe et al. | 604/397 |
| 4,578,066 | 3/1986 | O'Connor | 604/366 |
| 4,579,556 | 4/1986 | McFarland | 604/385 |
| 4,597,760 | 7/1986 | Buell | 604/397 |
| 4,597,761 | 7/1986 | Buell | 604/397 |
| 4,617,022 | 10/1986 | Pigneul et al. | 604/391 |
| 4,636,207 | 1/1987 | Buell | 604/370 |
| 4,673,402 | 6/1987 | Weisman et al. | 604/368 |
| 4,699,823 | 10/1987 | Kellenberger et al. | 428/219 |
| 4,728,326 | 3/1988 | Gilles | 604/391 |
| 4,822,435 | 4/1989 | Igaue et al. | 156/164 |
| 4,834,736 | 5/1989 | Boland et al. | 604/385 |
| 4,834,740 | 5/1989 | Suzuki et al. | 604/385 |
| 4,900,317 | 2/1990 | Buell | 604/370 |
| 4,964,860 | 10/1990 | Gipson et al. | 604/392 X |

FOREIGN PATENT DOCUMENTS

| | | |
|---|---|---|
| 0287388 | 10/1988 | European Pat. Off. . |
| 2566631 | 1/1986 | France . |
| 2165457 | 4/1986 | United Kingdom . |
| 2214057 | 8/1989 | United Kingdom . |

*Primary Examiner*—Randall L. Green
*Assistant Examiner*—D. Willse
*Attorney, Agent, or Firm*—Jeremiah J. Duggan

[57] ABSTRACT

A diaper comprises a rectangular disposable chassis assembly capable of absorbing and containing bodily wastes, including front, crotch and rear portions and a liquid-previous liner and liquid-impermeable barrier formed together about a liquid-absorbing core. A reusable elasticized cloth belt is removably retained by the chassis assembly, holding the diaper in place against the body during use. When fastened about a wearer, the belt provides a line of support extending transversely across the body of the core in the front portion of the chassis assembly corresponding to the lower abdominal region of the wearer. The belt cinches to snugly position the chassis assembly for absorbing discharged wastes. Preferably, the core contains a lower pledget with hydrogel that swells outwardly against the belt. Breathable elasticized leg cuffs extend along the side margins of the chassis assembly.

23 Claims, 4 Drawing Sheets

DIAPER HAVING DISPOSABLE CHASSIS ASSEMBLY AND REUSEABLE ELASTICIZED BELT REMOVABLY RETAINED BY SAID CHASSIS ASSEMBLY

This is a continuation of copending application Ser. No. 07/504,159 filed on 04/02/90, now abandoned.

TECHNICAL FIELD

The invention relates generally to diapers and, more particularly, to diapers having disposable absorbent assemblies which are positioned on the body by means of reusable belts.

BACKGROUND

There exists a need for diapers having a disposable absorbent assembly which can be effectively and inexpensively positioned by a simple reusable belt to hold the absorbent in place on the body, without the necessity for fastening elements manufactured on the absorbent assembly which add cost to the disposable absorbent assembly of the diapering system.

Multi-component diapering systems, i.e., diapers having disposable and reusable components, are well known in the art and are discussed in U.S. Pat. No. 4,834,736 to Boland, et al. Certain of these prior art diaper constructions have sought to provide waste containment with a reusable holder for retaining the absorbent structure, for example:

1) U.S. Pat. No. 3,658,064 to Pociluyko;
2) U.S. Pat. No. 3,370,590 to Hokanson, et al.;
3) U.S. Pat. No. 4,425,128 to Motomura;
4) U.S. Pat. No. 2,141,105 to Eller;
5) U.S. Pat. No. 4,397,646 to Daniels, et al.;
6) U.S. Pat. No. 4,597,761 to Buell;
7) U.S. Pat. No. 4,496,360 to Joffe, et al.; and
8) U.S. Pat. No. 4,597,760 to Buell.

Generally, the above-listed prior diaper constructions employ fastening elements that are integral with, i.e. nonseparable from the holder.

Unitary, i.e., one-piece constructions typically include an assembly of a liquid-impervious back sheet, a liquid-pervious liner and an absorbent core sandwiched between the liner and back sheet. The assembly defines either a modified hourglass shape, an I-shape, a rectangular shape or a T-shape and is secured about the wearer by means of adhesive tapes, hook-and-pile fasteners or the like. The entire diaper is disposable. In other words, the absorbent structure is not separable from other components of the diaper. Examples of such unitary constructions are discussed in the aforementioned U.S. Pat. No. 4,834,736, and are also disclosed in:

1) U.S. Pat. No. 4,324,245 to Mesek, et al.;
2) U.S. Pat. No. 3,196,874 to Hrubecky; and
3) U.S. Pat. No. 4,050,462 to Woon, et al.

Disposable diapers of the unitary type are flat or contoured, open-sided garments that are intended to be fit around an infant by a parent while the infant is lying down. The rear panel of the diaper is placed underneath the infant, and the front panel drawn between the infant's legs, after which the rear sides or "ears" are overlapped across the front panel and held together by the securement means described above.

Another approach taken by prior art diapers has been to utilize belts with absorbent structures in various combinations, for example: 1) British Patent No. 2,165,457; 2) French Patent No. 2,566,631; and 3) European Patent Application No. 0,287,388. The British '457 patent shows a disposable incontinence garment having an hourglass shape with a pair of flexible waistbands and a pair of elastic leg bands. A flexible tape is threaded through slits in the absorbent structure and secured together with hook-and-loop fasteners—neither the waistbands nor the tape of this diaper are elasticized. The French '631 patent discloses a unitary disposable elastic-legged diaper having an elasticized belt which is integral with, i.e., nonremovable from the rear waistband. Slits are formed in the front of the absorbent through which the free ends of the belt are threaded. The belt is not reusable. Similarly, the European '388 patent publication discloses a disposable absorbent garment with a pair of straps formed from the longitudinal margins of the garment, each strap having one end fixed to an end of the garment and another end which is attached to the front of the diaper.

U.S. Pat. Nos. 4,315,508 to Bolick and 4,617,022 to Pigneul, et al. both disclose multiple use garment suspension systems. The Bolick patent shows a pair of elastic suspension belts fastenable at their ends to corners of an absorbent structure. The Pigneul patent shows a single belt fastenable at its ends to the outer surfaces of the rear ears by means of hook-and-pile tapes. The singular belt extends across and engages a grip on the outer surface of the front of the diaper.

Other prior art constructions are depicted in U.S. Design Pat. Nos. 121,647; 132,937; 290,780; and 306,209.

SUMMARY OF THE INVENTION AND ADVANTAGES

According to the invention, a diaper article comprises a disposable absorbent chassis assembly having a liquid-pervious body-facing sheet, a substantially liquid-impervious backing sheet and a liquid-absorbing core contained between the backing and facing sheets. Front, crotch and rear portions of the chassis assembly are disposed along a longitudinal axis. A pair of side margins extend generally parallel to the longitudinal axis, and front and rear end margins extend generally transverse to the longitudinal axis. A reusable elasticized belt, separable from the chassis assembly, has free ends releasably engagable with one another. Means are provided on the front and rear portions of the chassis for removably retaining the belt in liquid isolation from the core when the ends are engaged about the torso of a wearer in use. When fastened, the belt defines a line of support extending across the body of the core in the front portion of the chassis assembly which line corresponds to the lower abdominal region of the wearer, the belt being cinched to securely position the chassis assembly for the absorbing of discharged bodily wastes.

An advantage of the invention is that an economical disposable absorbent chassis is utilized which need not be equipped with integral, i.e., factory-installed fasteners, tapes or the like for the purposes of securement about the body. Rather, the absorbent chassis conveniently and simply functions with the reusable belt, being comfortably yet securely held in position against the body. Because the belt is reusable, only the absorbent chassis need be disposed of, allowing the belt to be fabricated from longer-lived materials of higher quality.

Another advantage of the invention is that the belt snugly fits the absorbent chassis against a wearer, ameliorating the frontal droop which tends to occur in diapers when the absorbent material becomes wet and heavy. This is accomplished by the belt applying a line of support transversely across the body of the core located in the front portion of the chassis. The downward gravitational forces exerted by a wetted absorbent assembly causes the belt to cinch and snugly hold the absorbent assembly in place against the wearer's body.

BRIEF DESCRIPTION OF THE DRAWINGS

The invention will be more fully understood and further advantages will become apparent when reference is made to the following detailed description and accompanying drawings in which.

DETAILED DESCRIPTION OF ONE OR MORE PREFERRED EMBODIMENTS

"Diapers" are articles, or portions of articles, which absorb and contain urinary and fecal wastes discharged from the body. The absorbent structures of the diapers are intended to be "disposable", i.e., discarded after a limited period of use and not laundered or otherwise restored for reuse. The absorbent structures of diapers are placed against the body of the wearer to absorb and contain the various bodily wastes which are discharged.

Figure 1:
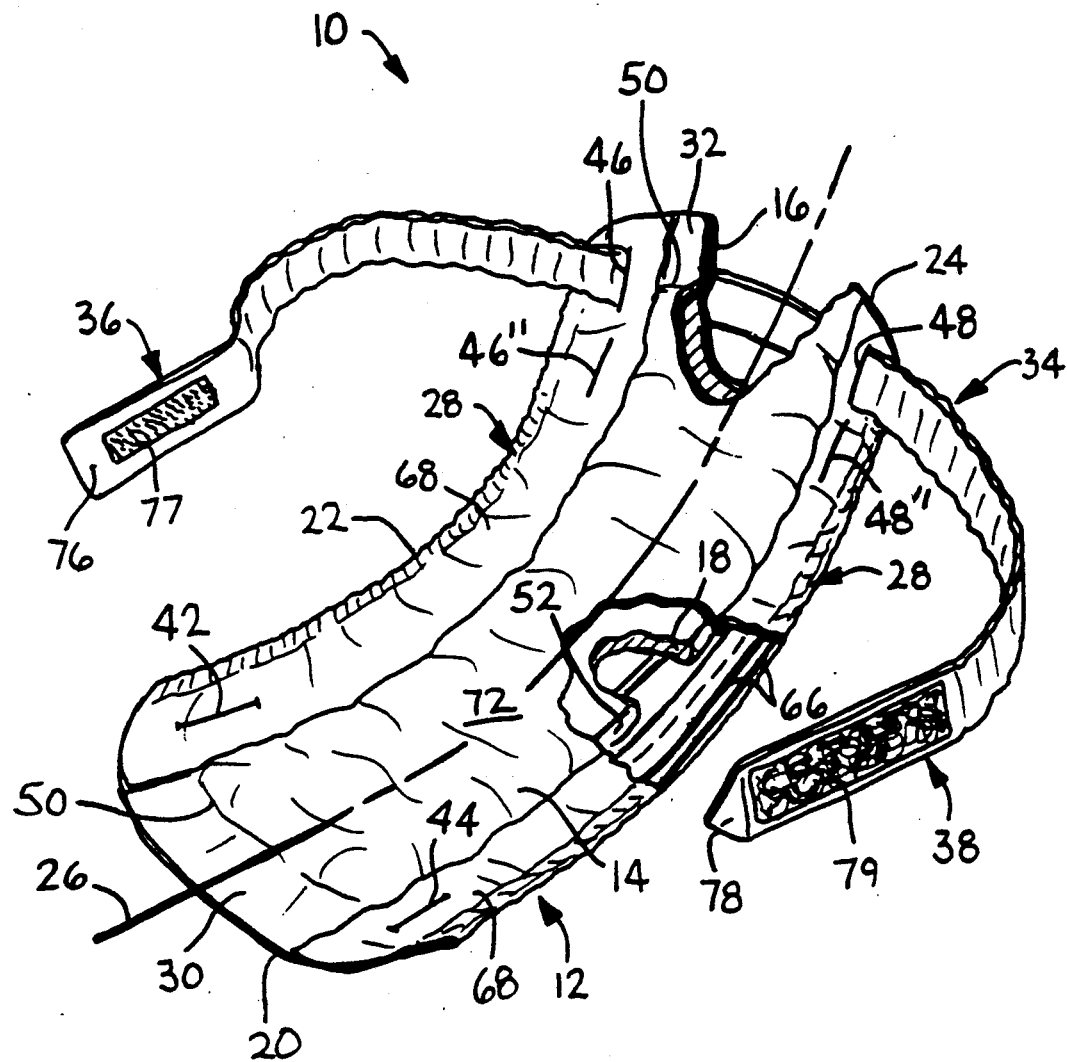
FIG. 1 is a perspective view showing the inside of a disposable diaper embodiment of the present invention, wherein a portion of the top sheet has been cut away to more clearly show the underlying structure of the absorbent chassis assembly, and also the relationship of the removable and reusable belt to the chassis assembly.
Figure 4:
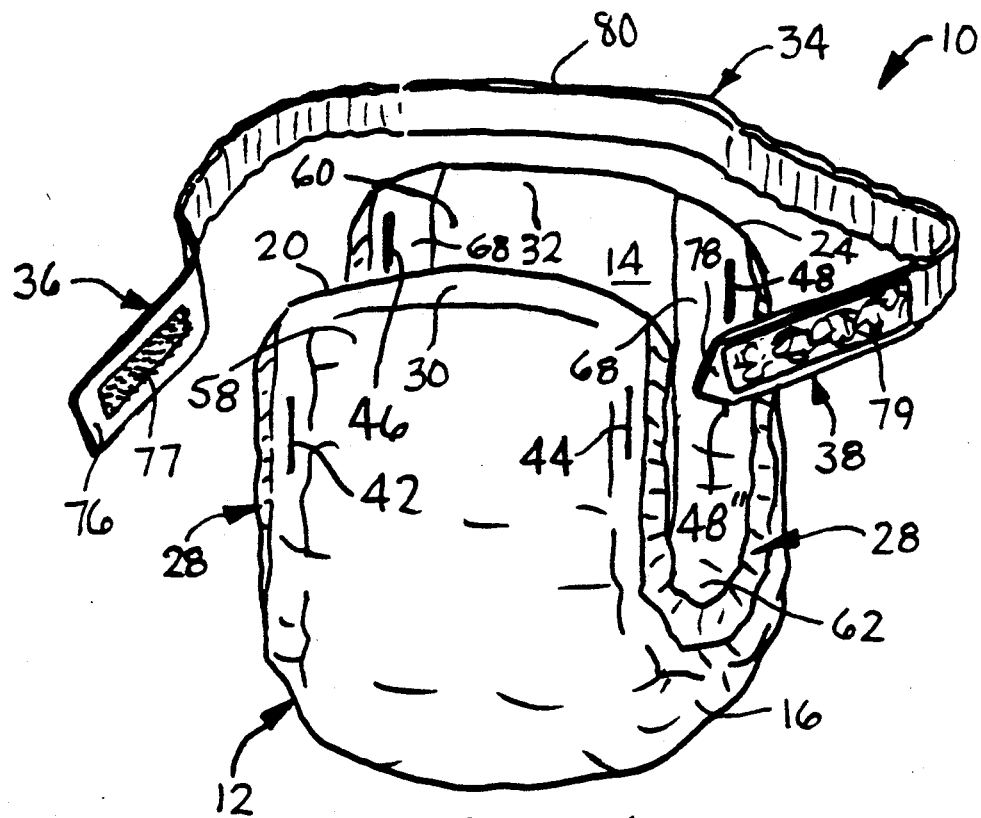
FIG. 4 is a perspective view of the present diaper, showing the belt separated from the chassis assembly.
Figure 5:
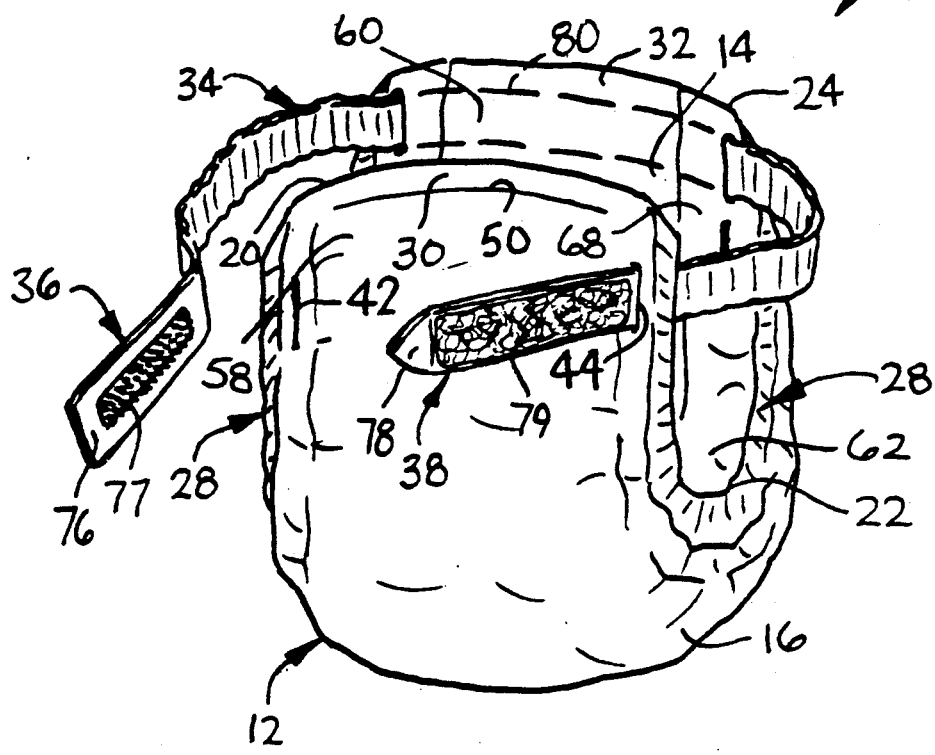
FIG. 5 is a view of FIG. 4, showing the belt being sequentially threaded through a retaining means of the present chassis assembly prior to being fastened together.
Figure 6:
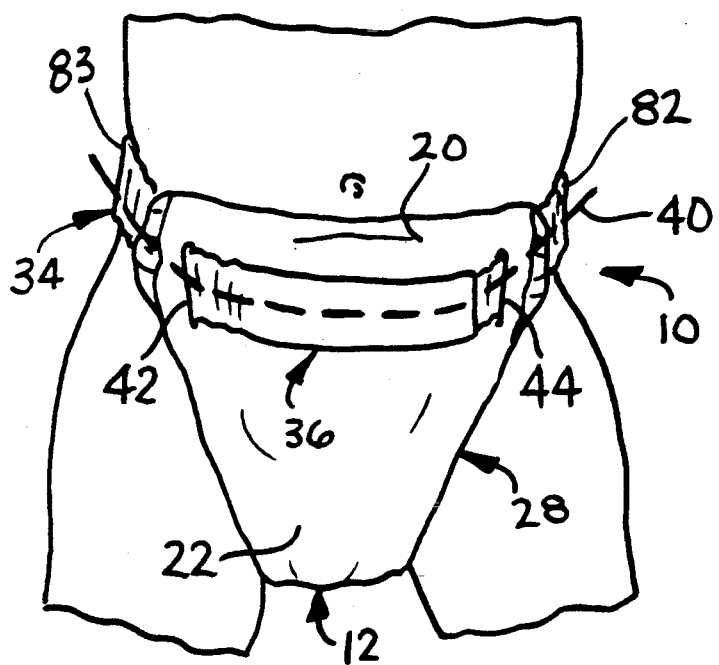
FIG. 6 is a front view of the present diaper shown secured around a baby, particularly the positioning of the chassis assembly relative to the baby's torso.

Referring to FIGS. 1, 4, and 5, a diaper 10 is generally shown. The diaper 10 comprises two pieces which are separable from one another. First, an absorbent chassis assembly, generally shown at 12, has a generally rectangular shape. The chassis 12 comprises a liquid-pervious body-facing sheet 14, a liquid-impervious backing sheet 16 and a liquid-absorbing core 18 contained between the facing 14 and backing 16 sheets. The chassis assembly 12 has front 20, crotch 22, and rear 24 portions disposed along a longitudinal axis 26. A pair of flexible side margins 28, which are preferably gathered, extend generally parallel to the longitudinal axis 26, with front 30 and rear 32 end margins extending generally transverse to the longitudinal axis 26. Secondly, a reusable elasticized belt, generally shown at 34, has free ends 36, 38 releasably engagable with one another. The belt 34 is retained on the front 20 and rear 24 portions in liquid isolation from the core 18 during use, defining a line of support 40, best shown in FIGS. 6 and 7, extending across the body of the core 18 in the front portion 20 of the chassis assembly 12, and corresponding to the lower abdominal region of the wearer. Thus, the belt 34 functions to snugly position the chassis assembly 12 against the body to absorb wastes discharged in use.

In FIGS. 1 and 4–7, there is shown a preferred embodiment of the invention. The belt 34 is retained on the front 20 and rear 24 portions of the chassis assembly 12 by means which comprise longitudinally extending pairs of front 42, 44, and rear 46, 48 fenestrations formed in the side margins 28 of the chassis assembly 12. The belt 34 is threaded through the fenestrations 42, 44, 46, 48, as shown in FIGS. 4–7, and the ends 36, 38 of the belt 34 are then engaged with one another about a wearer, as further shown in FIGS. 6–7. The rear fenestrations 46, 48 are located longitudinally above a seal 50 formed about the peripheral edge 52 of the core 18 adjacent the rear end margin 32 (FIG. 1). An additional pair of rear fenestrations 46'', 48'' are located below the seal line 50 in the rearward areas 60 of the opposed side margins 28 to provide an adjustable fit to the diaper 10 over a range of body sizes. The additional pairs of rear fenestrations 46'', 48'' are also spaced longitudinally a selected distance from the rear fenestrations 46, 48 which are located nearest the rear margin 32. As a result, the rear waist margin 32 may be folded-over outwardly, i.e., away from the wearer's body, and down along the seal line 50 to align the respective longitudinally-spaced pairs of rear fenestrations 46, 46'' and 48, 48'' with one another and allow the belt 34 to be threaded (not shown) through the aligned rear fenestrations 46, 46'' and 48, 48''. Thus, by utilizing the additional pair of fenestrations 46'', 48'' in this manner, the diaper 10 can be adapted to fit various body sizes. The front fenestrations 42, 44 are located below the seal 50 adjacent the front end margin 30 so that the belt 34 extends across the body of the core 18 in the front portion 20 of the chassis assembly 12 when threaded through the front pair of fenestrations 42, 44 in use. Alternatively, it can be appreciated that other retaining means may be employed besides the fenestrations 42, 44, 46, 48. For example, loops (not shown) could each be formed in the side margins of the chassis assembly from a pair of closely spaced side-by-side slits, such that the material spacing each pair of slits apart from one another forms a loop for retaining the belt when it is routed through the loop. Another possible alternative retaining means could comprise a hem (not shown) formed, for example, by a folded-over portion of a diaper backing sheet extending longitudinally from either or both of the front and rear end margins.

Referring to FIGS. 1 and 3A–3C, the body facing sheet 14 and the backing sheet 16 are attached together manner about the peripheral edge 52 of the absorbent core 18, such as by the seal 50. The body facing sheet 14 is affixed directly to the backing sheet 16, although other, alternative configurations are possible. For example, the facing sheet 14 may be joined to the backing sheet 16 by affixing the facing sheet 14 to intermediate members (not shown) Which, in turn, are affixed to the backing sheet 16. The facing sheet 14 and the backing sheet 16 can be affixed directly to each other in the side margins 28 and end margins 30, 32 about the periphery 52 of the core 18 by a variety of attachment means known in the art, for example, adhesive bonds, sonic bonds and/or thermal bonds. For example, a continuous uniform layer of adhesive, a patterned layer of adhesive, or an array of separate lines or spots of construction adhesive may be used to affix the facing sheet 14 to the backing sheet 16.

Preferably, the facing sheet 14 and the backing sheet 16 are adhesively joined to one another along the seal line 50 (FIGS. 1 and 3A) about the peripheral edge 52 of the core 18, the chassis assembly 12 having a generally rectangular-shape. The seal 50 retards leakage of liquid from the core 18 into the side margins 28 and end margins 30, 32 of the chassis assembly 12. Although the belt 34 is threaded through the absorbent chassis assembly 12 as described, the belt 34 does not become soiled by the liquids absorbed into the core 18. Rather, as shown in FIG. 5, the belt 34 extends across the outside of the liquid-impermeable backing sheet 16 as the belt 34 surrounds the body of the core 18, particularly in the front portion 20 of the chassis assembly 12. Because liquid does not typically escape from the core 18 adjacent the fenestrations 42, 44, 46, 48, which are formed in the side margins 28 outboard of the core is, the belt 34 is isolated from liquid contact by the backing sheet 16.

Figure 2:
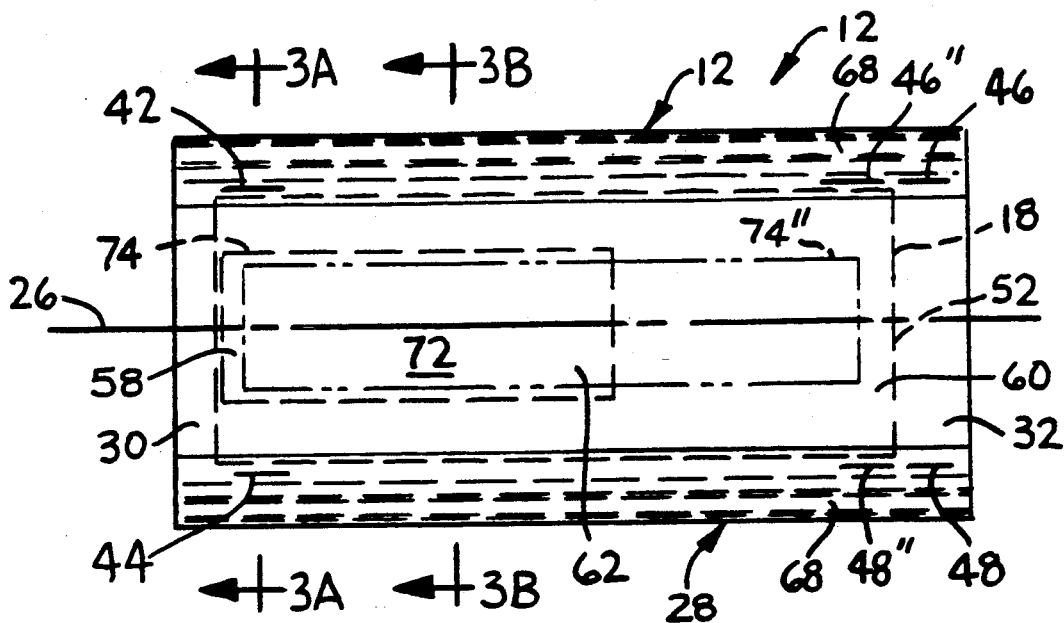
FIG. 2 is a top plan view showing the absorbent chassis assembly of the present diaper in a flat-out condition.

FIG. 2 is a representative plan view of the inside of the diaper 10 of the present invention in its flat-out uncontracted state (i.e., with any elastic in an extended state). The body facing sheet 14 and the backing sheet 16 are generally rectangular and coextensive in length and width dimensions (i.e., in the longitudinal and transverse directions, respectively), and are generally larger than those of the absorbent core 18. The top body-facing sheet 14 is associated with and superimposed on the back sheet 16 about the core 18 which has a generally rectangular shape. The end margins 30, 32 respectively extend beyond the peripheral edge 52 of the core 18 a distance from about 2 percent to about 20 percent of the length of the chassis assembly 12. Preferably, the front margin 30 extends about 5 percent, and the rear margin 32 extends about 20 percent of the length of the entire chassis assembly 12. When the diaper 10 is worn, the front end margin 30, partially covers the front lower torso, and the rear margin 32 covers the back waist of the wearer. The side margins 28 each have forward 58, rearward 60, and crotch 62 areas which extend parallel to the longitudinal axis 26 outboard of the peripheral edge 52 of the core 11.

An advantage of the rectangular shape is that considerable waste is eliminated during manufacture on present diaper converting equipment. Specifically, the majority of present diaper converting equipment is designed to form singular diaper batts in end-to-end fashion and then trim the batts with leg cut-outs to achieve a contoured shape prior to assembling the finished product. This procedure entails waste and process complexity not required in manufacturing diapers of the present invention. Notwithstanding, modified hourglass, I-shaped or T-shaped configurations of the chassis assembly are within the scope of this invention, although these shapes would have the attendant disadvantages discussed above.

As shown in FIGS. 2 and 3A-C, the pair of side margins 28 are gathered by the elasticized leg cuffs 64. The elasticized leg cuffs 64 are adapted to contact the wearer's inner thighs, resulting in a form-fitting appearance and reducing leakage sideways at the crotch portion 22. The elastic leg cuffs 64 extend the entire length of the side margins 28 and are secured to the chassis assembly 12 in an elastically contractible, or stretched condition so that in a normal, unrestrained configuration, the leg cuffs 64 contract against the chassis assembly 12. Elastic members, preferably threads 66, elasticize the leg cuffs 64 and extend the length of the leg cuffs 64, or may be any other length selected to provide the arrangement of elastically contractible lines desired for a particular diaper design. As shown, a pair of relatively thin elastic threads 66 are used, for example, a material sold by DuPont as Lycra® having a width less than 0.25 mm per thread, which are applied to the fabric strip 68 of the leg cuffs 64 in a tensioned state. Other types of elastic members may be used rather than or in addition to the threads 66, for example, heat-shrinkable materials could be used which are not tensioned when applied, but instead are rendered elastically contractible by the application of heat.

Figure 3A:
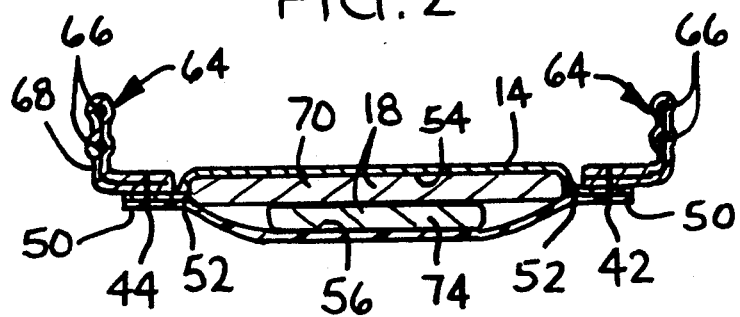
FIG. 3A is a cross-sectional view of FIG. 2, taken along sectional lines 3A—3A, showing a breathable leg cuff of the present invention.
Figure 3B:
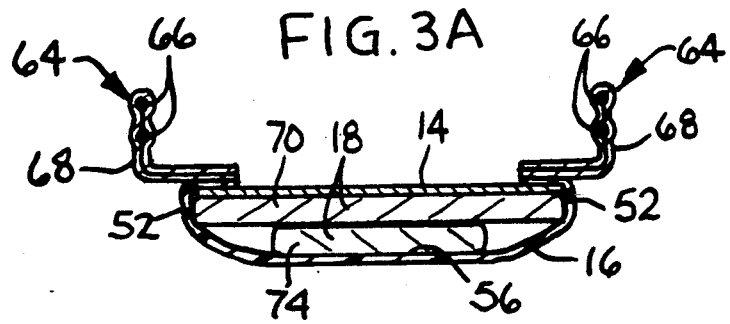
FIG. 3B is a cross-sectional view of FIG. 2, taken along sectional lines 3B—3B, showing an alternative embodiment of the breathable leg cuff of the present invention.

The elastic leg cuffs 64 may have a number of different configurations. Although the width the individual elastic threads 66 described above is preferably about 0.25 millimeters (0.01 inches) or less; other elastic members may be used having widths varying up to 25 millimeters (1.0 inches) or more. The elastic members may comprise a single band of material, but preferably comprise several threads 66. The elastic members 66, as well as the separate leg cuffs 64, as shown in FIGS. 3A and 3B, may be affixed to the chassis assembly 12 in any of several ways which are known in the art. For example, the elastic members 66 may be ultrasonically bonded, heat or pressure-sealed using a variety of bonding patterns; preferably, adhesive bonding is used. The elastic threads 66 and/or the leg cuffs 64 may be respectively applied in either a rectilinear (shown) or curvilinear (not shown) fashion.

Figure 3C:
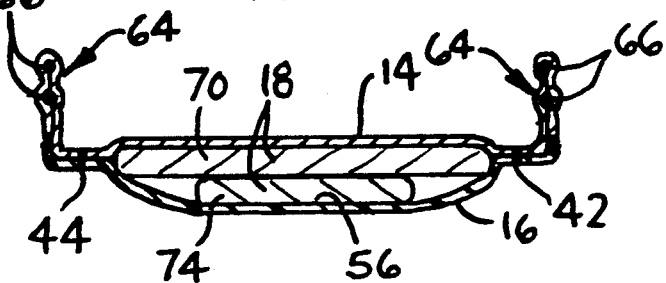
FIG. 3C is a cross-sectional view, taken along sectional lines 3A—3A, showing another alternative embodiment of the breathable leg cuff of the present invention.

As shown in FIGS. 3A-B, the leg cuffs 64 comprise separate pieces joined to the chassis 12; in FIG. 3C integral co-extensions of the backing 16 and facing 14 sheets form leg cuffs 64. In either case, the leg cuffs 64 extend laterally outboard of the peripheral edge 52 of the core Is over substantially the entire length of the chassis assembly 12. Therefore, the side margins 28 generally comprise the leg cuffs 64. The end margins 30, 32 are each formed by longitudinal co-extensions of the backing 16 and facing 14 sheets beyond the peripheral edge 52 of the core 18.

The fabric strips 68, to which the elastic bands 66 are applied in forming the leg cuffs 64, are preferably comprised of a soft and "breathable", i.e., gas-permeable, fibrous web. The degree of gas-permeability may be controlled by the proper selection of web characteristics, by treatment of the web or by other obvious design choices. The elastic threads 66 are applied to fabric strips 68 such as a spun-bonded web, which are then joined longitudinally to the liquid-pervious body-facing sheet 14 as shown in FIG. 3A. Alternatively, the leg cuff 64 can be formed as shown in FIG. 3B, wherein the liquid-impervious backing sheet 16 is C-folded over the shoulder of the peripheral edge 52 of the core 18 and joined to the facing sheet 14. The fabric strips 68 are, in turn, joined to the backing sheet 16 along the shoulder of the core 18. As previously indicated with respect to FIG. 30, the leg cuff 64 may comprise co-extensions of the backing 16 and facing 14 sheets, which extend laterally outboard of the peripheral edge 52 of the core 18. Generally, the amount of impermeable material which comprises the leg cuffs 64 may be varied in a number of ways in order to obtain the desired degree of breathability. A preferred well-known method for modifying the breathability of the leg cuffs 64 is to extend the backing sheet 16 outboard of the peripheral edge 52 of the core 18 a selected distance. Alternatively, various web surface treatments may be used to achieve a similar purpose.

Referring specifically to FIGS. 2, 3A and 3C, the multiple thicknesses of material in the side margins 28 serve to withstand tensile stresses exerted on the material surrounding the fenestrations 42, 44, 46, 48. Particularly, the various layers which comprise the leg cuffs 64, serve as reinforcements for the front pair of fenestrations 42, 44, and likewise for the rear pair of fenestrations 46, 48. With respect to FIGS. 3A and 3B, the leg cuffs 64 each comprise a double thickness of fabric strip 68 which is joined to the chassis 12 to comprise the side margins 28. The fenestrations 42, 44, 46, 48 extend in a longitudinal direction to accommodate the width dimension of the belt 34 as it is being threaded through the fenestrations 42, 44, 46, 48, so that tensile forces are taken up by the belt rather than by the chassis 12.

As shown in FIGS. 1 and 3-5, the leg cuffs 64 are constrained to assume an upstanding configuration relative to the surface of the body facing sheet 14, flexibly conforming to the inner thighs and gathering the crotch portion 22 of the chassis assembly 12 into a boat-shape between the legs of a wearer to help provide a snug fit. The flexible leg cuffs 64 continually gasket the inner thighs of the wearer to retard leakage from the side margins 28 of the absorbent chassis assembly 12. It is preferred that each of the elastically contractible threads 66 exert a tensile force on the associated leg cuff 64 from about 20 to 30 grams, so that each pair of threads 66 collectively exerts a generally longitudinal tensile force from about 40 to 60 grams per leg cuff 64.

As best shown in FIGS. 1 and 2, the core 18 preferably comprises a multi-layered absorbent structure. A top fluid acquisition layer 70, situated between the end margins 30, 32 and side margins 28, has a fluid target zone 72 (FIGS. and 2) which absorbs fluids deposited on the body facing sheet 14 along the top face 54 of the top layer 70. A bottom fluid storage layer 74, preferably formed substantially separately from the top layer 70, receives liquid transferred from the top layer and stores the liquid remotely from the wearer's skin. It should be understood that either or both of the constituent layers 70, 74 which preferably comprise the core 18 could be singularly or collectively wrapped in tissue layers (not shown), as the case may be.

The layers 70, 74 of the core 18 shown in FIGS. 1-3 each comprise hydrophilic fibers, preferably a cellulosic fluff, of which many different forms are available commercially. Various types of wettable, hydrophilic fibrous material can be used in the component parts of the absorbent core 18. Examples of suitable fibers include naturally occurring organic fibers composed of intrinsically wettable materials, such as the cellulosic fibers which are preferred; synthetic fibers composed of cellulose; or cellulose derivatives such as rayon fibers. Suitable cellulosic fibers can be obtained from Kimberly-Clark Corporation as CR-54 ® or Long-Lac ® as pulp sheets, then may be fiberized by any of a variety of conventional hammermill techniques known in the art. The size and absorbent capacity of the core 18 should be compatible with the size of the intended wearer, and the liquid load imparted by the intended use of the diaper. Further, the size and the absorbent capacity of the absorbent core 18 can be varied to accommodate wearers ranging from infants through adults. In addition, it has been found that with the present invention, the densities and/or basis weights of the respective layers 70, 74 can be varied.

The relative dimensions of the various portions of the chassis assembly 12, and particularly of the absorbent core 18, can be varied depending on materials used and the desired product needs. Although a target zone 72 is designated toward the front portion 20 of the absorbent assembly 12 in FIGS. 1 and 2, the target zone 72 may be offset to encompass the particular location where liquid is discharged. For example, male infants tend to urinate further toward the front portion 20 of the absorbent chassis assembly 12. The female target zone (not shown) is located closer to the center of the crotch portion 22. As a result, the shape and relative longitudinal placement of the lower layer 74 can be selected to best correspond with the actual target zone of either or both categories of wearers. As shown, the core 18 comprises a discrete pledget 74, underlying the top layer 70 and dimensionally shorter and narrower than the top layer 70. Alternatively, the bottom layer 74" may extend substantially the entire length of the top layer 70.

The use and placement of the discrete pledget 74 according to the present invention lessens the total amount, hence the cost, of absorbent material which is adequate to meet the absorbent capacity needs of a given user. This is because placement of the hydrogel-containing discrete pledget 74 more efficiently utilizes the absorbent capacity of the core 18 in the front one-half of the diaper 10. The pledget 74 preferably comprises hydrophilic fibers, such as cellulosic fluff, mixed with absorbent gelling particles, i.e., hydrogel, which have a high retention capacity, even under compressive loads applied in use. In other arrangements, the pledget 74 may comprise a mixture of superabsorbent hydrogel particles and synthetic polymer meltblown fibers, or a mixture of superabsorbent particles with a fibrous co-form material comprising a blend of natural fibers and/or synthetic polymer fibers. The top layer 70 preferably comprises cellulosic fibers and is substantially free of absorbent gelling particles at least in the target zone 72. This construction enables the top layer 70 to more freely acquire and distribute fluids and transfer those fluids throughout the top layer 70 and especially to the underlying pledget 74. This construction has been found to result in relatively high rates of utilization of the total absorbent capacity of the core 18.

Another advantage of the present absorbent chassis 12 is that placement of absorbent gelling material in the front portion 20 of the chassis assembly 12 provides an even more effective barrier against forward migration of feces into the genital region of a wearer when the hydrogel becomes swollen following urination.

Suitable absorbent gelling materials can be organic materials such as silica gels or organic compounds such as cross-linked polymers. Cross-linking may be covalent, ionic, Van der Waals, or hydrogen bonding. Examples of absorbent gelling material polymers and copolymers include polyacrylamides, polyvinyl alcohol, ethylene maleic anhydride copolymers, polyvinyl ethers, hydroxypropyl cellulose, carboxymal methyl cellulose, polyvinylmorpholinone, vinyl sulfonic acid, polyacrylates, polyacrylamides, polyvinyl pyrrolidone, and the like. Other polymers suitable for use in the absorbent core 18 include hydrolyzed acrylonitrile grafted starch, acrylic acid grafted starch, polyacrylates and isobutylene maleic anhydride copolymers or mixtures thereof. Still other suitable hydrogels are disclosed by Assarson, et al. in U.S. Pat. No. 3,902,236 issued Aug. 26, 1975. Processes for preparing hydrogels are disclosed in U.S. Pat. No. 4,076,663 issued Feb. 28, 1978, to Masuda, et al. and U.S. Pat. No. 4,286,082 issued Aug. 25, 1981, to Tsubakimoto, et al. As mentioned previously, the absorbent gelling material used in the absorbent core Is and most preferably in the pledget 74, is generally in the form of discrete particles. The particles may be of any desired shape, for example, spiral or semi-spiral, cubic, rod-like, polyhedra, etc. Shapes having a large greatest dimension/smallest dimension ratio, like needles, flakes, and fibers, are also contemplated for use herein. Conglomerates of particles of absorbent gelling material may also be used, for example, in the pledget 70 shown in FIGS. 1-3.

As discussed above, the hydrogel in the absorbent core 18 shown in FIGS. 2, 3A, and 3B, is concentrated in a separate bottom pledget layer 74, such that the majority of the hydrogel is concentrated in the thickness or Z-axis direction of the core 18 towards the back face 56. An alternative embodiment (not shown) to this construction would be to form the core 18 of a continuous mixture of hydrophilic fibers and absorbent gelling particles in a unitary layer such that there is a gradient of hydrogel particles concentrated toward the back face of the unitary layer. Such a Z-gradient concentration of absorbent gelling particles in a unitary cellulosic layer is taught by U.S. Pat. No. 4,699,823 to Kellenberger, issued Oct. 13, 1987. Still another alternative construction of the absorbent core (not shown) is to deposit a discrete layer of hydrogel particles within the absorbent core, either between separate layers of a multi-layer core, as contemplated by the embodiments of FIGS. 2, 3A, and 3B, or internally within a unitary core as taught in the aforementioned U.S. Pat. No. 4,699,823.

Figure 7:
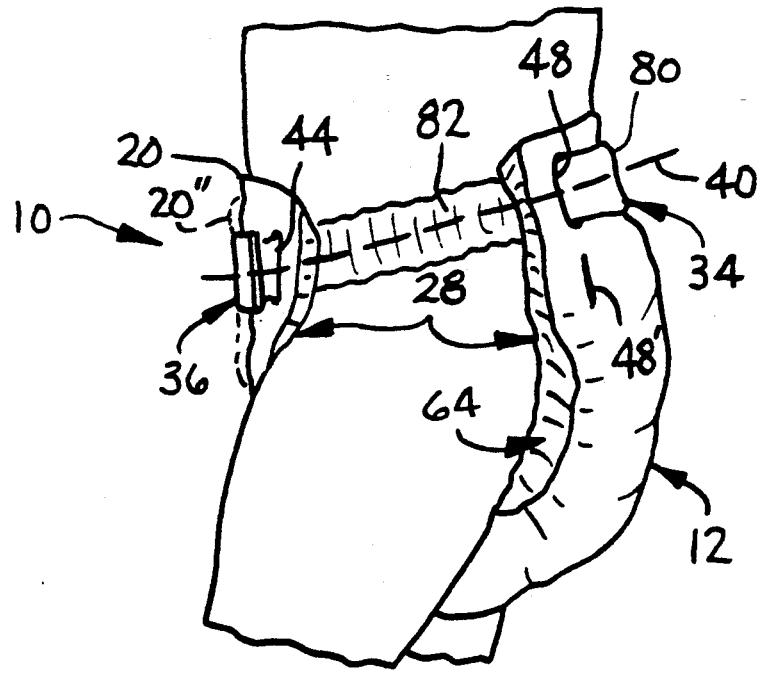
FIG. 7 is a side view of the present diaper shown secured around a baby.

The liquid thus absorbed into the core 18 is contained toward the back face 56 of the core 18, thereby more effectively isolating liquid from the wearer and causing the hydrogel particles to swell and exert an outward pressure against the backing sheet 16 and the belt 34, as shown in FIG. 7. The belt 34 effectively "cinches" by exerting an opposing tensile force against the body of the absorbent core 18 in the front portion 20 of the chassis assembly 12, as indicated in phantom at 20, in response to pressure from the swollen hydrogel, thereby holding the absorbent chassis assembly 12 snugly in place during continued use. This "cinching" of the belt 34 forces the absorbent material located axially between the belt 34 and the wearer's skin, especially the hydrogel, to redistribute its mass among the upper thigh contours.

The body-facing sheet 14 presents a surface which is compliant, soft-feeling, and nonirritating to the wearer's skin. Further, the facing sheet 14 is sufficiently porous to be liquid pervious, permitting liquid to readily penetrate through its thickness. A wetting agent may be used, depending on the porosity of the facing sheet 14, in order to facilitate liquid penetration through the sheet 14. A suitable facing sheet 14 may be manufactured from a wide range of web materials, such as porous films, reticulated films, apertured plastic films, natural fibers (for example, wood or cotton fibers), synthetic fibers (for example, polyester or polypropylene fibers), or a combination of natural and synthetic fibers. The facing sheet 14 is typically employed to help isolate the wearer's skin from liquids held in the absorbent core 18. Various woven and nonwoven fabrics can be used for the facing sheet 14. For example, the body-facing sheet 14 may be composed of a meltblown or spunbonded web of polyolefin fibers. The body-facing sheet I4 may also be a bonded-carded-web composed of natural and synthetic fibers. The term "nonwoven web" means a web of material which is formed without the aid of a textile weaving or knitting process. The term "fabrics" is used to refer to all of the woven, knitted and nonwoven fibrous webs.

The backing sheet 16 is substantially impervious to liquids and is typically manufactured from a thin plastic film, or other flexible liquid-impervious material. As used in the present specification, the term "flexible" refers to materials which are compliant and which will readily conform to the general shape and contours of the wearer's body. The back sheet 30 substantially prevents the fluid contained in the absorbent core 18 from wetting articles such as bed sheets and overgarments which contact the diaper 10. In the shown embodiment, the back sheet 16 is a polyethylene film having a thickness of from about 0.12 millimeters 5 mil) to 0.051 millimeters (2.0 mils).

Alternatively, the back sheet may be a woven or nonwoven fibrous web layer which has been constructed or treated to impart the desired level of liquid impermeability. Back sheet 16 may optionally be composed of a "breathable" material which permits vapors to escape from the absorbent core 18 while still preventing liquid wastes from passing through the backing sheet 16, in order to further promote skin dryness of the wearer. The backing sheet 16 can also be embossed and/or matte finished to provide a more aesthetically pleasing appearance.

The size of the back sheet 16 is determined by the size of the absorbent core 18 and the exact diaper design selected. The backing sheet 16, for example, may have a generally T-shape, a generally I-shape or a modified hourglass shape as discussed above. However, the backing sheet 16 preferably has a generally rectangular shape corresponding to that of the chassis 12. The backing sheet 16 extends beyond the peripheral edge 52 of the absorbent core 18, particularly the top layer 70, by a selected distance to comprise the end margins 30, 32. The backing sheet as discussed above, may also extend beyond the peripheral edge 52 of the top layer 70 to partially form the side margins 28 (FIGS. 3A and 3C) or may not extend beyond the peripheral edge 52 FIG. 3B) in the side margins 28.

The belt 34 is preferably made of a fabric material which is capable of withstanding multiple diapering cycles, for example, a cloth fabric woven from any combination of natural or synthetic fibers, such as cotton and/or polyester yarns. Alternatively, a durable nonwoven fabric could comprise the belt 34, for example a needle-punched or stitch-bonded web. The belt 34 should be breathable, soft, and conformable to the wearer and is preferably launderable.

Referring to FIGS. 1 and 4-5, the mating surfaces 76 and 78 of the ends 36 and 38, respectively, present cooperating mechanical fastener closure means, preferably hook 77 and loop 79 tapes of the type manufactured by Velcro, USA, Inc. and long known in the art. Alternatively, the ends 36, 38 of the belt 34 could be releasably engaged with one another by means of buttons and button holes (not shown). For example, the outwardly-facing surface 78 of the end 38 could leave a button sewn thereon and the end 36 could have a plurality of button holes extending transverse to the longitudinal axis 26, i.e., along the length of the belt 34, to provide adjustability of the belt 34 at fixed positions. "Mechanical" fasteners are distinguishable here from adhesive or cohesive tapes, in terms of the ability of mechanical fastening devices to still fasten together even following contact with liquid, such as during a washing cycle. The belt 34 further comprises a central portion 80, extending transversely across the rear portion 24 of the chassis assembly 12 between the rear pair of fenestrations 46, 48, respectively. Preferably, the belt 34 is selectively elasticized along lateral portions 82, 83, which extend between the rear 46, 48 and front 42, 44 pairs of fenestrations, respectively, and which are those portions of the belt contacting the outer hip regions of a wearer in FIGS. 6 and 7. In other words, the bulky chassis 12 does not cover the wearer's torso over the outer hip region, hence, the diaper 10 is "open" along the lateral portions 82, 83 of the belt 34. Alternatively, the rear 80 and/or the end 36, 38 portions of the belt 34 could be elasticized in addition to or instead of the side portions 82, 83. A variety of elastic materials could be used, e.g., natural rubber, to elasticize the belt 34.

The tension of the belt 34 may be adjusted to the individual body size of the intended user, by means of the variable-position fastening closures described herein, to achieve the fit desired for the diaper 10.

Having thus described the invention in rather full detail, it will be readily apparent that various changes and modifications may be made without departing from the spirit of the invention. All of such changes and modifications are contemplated as being within the scope of the present invention, as defined by the claims.

We claim:

1. A diaper article comprising:
   a disposable absorbent chassis assembly having a liquid-pervious body-facing sheet; a substantially liquid-impervious backing sheet; a liquid-absorbing core contained between the backing and facing sheets; continuous front, crotch and rear portions disposed along a central longitudinal axis of the chassis assembly; a pair of side margins extending generally parallel to the longitudinal axis, each of the side margins having forward and rearward extending portions and front and rear end margins extending generally transverse to the longitudinal axis; the core having front and rear end margins extending transversely of the longitudinal axis;
   a reusable continuous elasticized belt adjustable in length separable from the chassis assembly and having a central portion and a pair of free ends releasably engagable with one another; and
   means on the front and rear portions of the chassis assembly for removably retaining the belt in fluid isolation from the core and, when the ends of the belt are engaged with one another about the torso of a wearer for defining a line of support which extends across and below the rear end margin of the chassis assembly and the front end margin of the body of the core in the front portion of the chassis assembly corresponding to the lower abdominal region of the wearer, the belt being cinched across and below the front end margin of the core to securely position the chassis assembly for the absorbing of bodily wastes discharged in use.

2. The diaper of claim 1 wherein the forward and rearward portions of the side margins of the chassis assembly do not extend completely about the torso and the belt further comprises a pair of lateral portions intermediate the central and end portions, respectively, and adapted to contact the torso therealong while interconnecting the forward and rearward portions of the side margins.

3. The diaper of claim 2 wherein the belt comprises a breathable fabric.

4. The diaper of claim 3 wherein the ends of the belt have cooperable mechanical closures which are adjustable to securely fit a range of body sizes.

5. The diaper of claim 4 wherein the mechanical closures comprise complementary hook-and-loop fastening tabs disposed on overlapping surfaces of the cooperating end portions of the belt.

6. The diaper of claim 1 wherein the size margins of the chassis assembly comprise elasticized leg cuffs between the forward and rearward portions.

7. The diaper of claim 6 wherein the leg cuffs are elasticized by a plurality of elastic threads.

8. The diaper of claim 7 wherein the leg cuffs comprise a breathable material.

9. The diaper of claim 8 wherein the breathable material of the leg cuffs comprises a nonwoven fabric which is liquid permeable.

10. The diaper of claim 8 wherein the leg cuffs cause the crotch area of the side margins to become upstanding from the surface of the body-facing sheet.

11. The diaper of claim 1 wherein the liquid-absorbing core comprises: a top fluid acquisition layer, situated between the end and side margins, the top layer defining a fluid target zone; and a bottom fluid storage layer containing a hydrogel, formed substantially separately from the top layer and in fluid communication with the top layer.

12. The diaper of claim 11 wherein the bottom storage layer comprises a discrete pledget having a lesser surface area than the top layer and being in liquid communication with the top layer.

13. A diaper article comprising:
    a disposable chassis assembly having a liquid-pervious body-side liner and a liquid-impervious barrier joined to one another about their peripheral edges and a liquid-absorbing core contained between the liner and barrier, the chassis assembly having continuous front, crotch and rear portions disposed along a central longitudinal axis, the core having a body face and a back face and containing a hydrogel concentrated toward the back face in at least the front portion of the chassis assembly, the core defining a generally rectangular shape having continuous front, crotch and rear portions disposed along the longitudinal axis with front and rear end margins each extending transversely to the axis; the chassis assembly having a pair of side margins each having forward, crotch and rearward areas which extend essentially parallel to the longitudinal axis outboard of the peripheral edges of the core and front and rear end margins extending transversely of the longitudinal axis, the crotch areas of the side margin being elasticized by a pair of gatherable leg cuffs; laterally aligned pairs of fenestrations formed at the forward and rearward areas of the side margins of the chassis assembly, respectively, the forward areas pair of fenestrations being longitudinally spaced below the front end margin of the core; and a reusable continuous elasticized belt adjustable in length which is separable from the chassis assembly, having an elongated central portion and a pair of free end portions which are engagable with one another, presenting cooperating mechanical closures, wherein the belt is adapted for being removably threaded through the forward and rearward areas pairs of fenestrations, engaging the central portion of the belt across the rear portion of the chassis assembly, and fastening the free end portions with one another across the front portion of the chassis assembly, providing a line of support extending across and below the rear end margin of the chassis assembly and the front end margin of the body of the core in the front portion of the chassis assembly corresponding to the lower abdominal region of a wearer, the belt being cinched across and below the front end margin of the core to securely position the chassis assembly against the wearer for absorbing discharged bodily wastes.

14. The diaper of claim 13 wherein the core has a top layer and a bottom layer, formed separately from the top layer, the bottom layer containing hydrogel.

15. A diaper article comprising:

disposable chassis assembly having a liquid-pervious body-facing liner and a liquid-impervious barrier joined to one another about their peripheral edges, and a liquid absorbent core contained between the liner and barrier, the chassis assembly having continuous front, crotch and rear portions disposed along a central longitudinal axis, the core defining a generally rectangular-shaped composite having continuous front, crotch and rear portions disposed along the longitudinal axis, and front and rear end margins each extending transversely to the longitudinal axis; the chassis assembly having a pair of side margins each having forward, crotch and rearward areas extending generally parallel to the longitudinal axis outboard of the peripheral edges of the core and front and rear end margins extending transversely of the longitudinal axis, the forward and rearward areas of the side margins of the chassis assembly each having laterally aligned pairs of fenestrations formed therein respectively, the forward pair of fenestrations being longitudinally spaced below the front end margin of the core; and a reusable continuous elasticized belt adjustable in length having an elongated central portion, and free end portions which are engagable with one another, the belt being removably threaded through the forward and rearward areas pairs of fenestrations engaging the central portion thereof across the rear portion of the chassis assembly and the free end portions with one another across the front portion of the chassis assembly, providing a line of support which extends across and below the rear end margin of the chassis assembly and the front end margin of the body of the core in the front portion of the chassis assembly corresponding to the lower abdominal region of a wearer, the belt being cinched across and below the front end margin of the core to securely position the chassis assembly for the absorbing of bodily wastes discharged in use.

16. The diaper of claim 15 wherein the forward and rearward portions of the side margins of the chassis assembly do not extend completely about the torso, and the belt is selectively elasticized along a pair of elongated lateral portions, extending intermediate the central and end portions, respectively, adapted to contact the wearer's skin while interconnecting the forward and rearward portions of the side margins of the chassis assembly.

17. The diaper of claim 16 wherein the belt comprises a breathable fabric which is capable of withstanding multiple launderings.

18. The diaper of claim 17 wherein the end portions of the belt present cooperable mechanical closures which are adjustable to securely fit a range of body sizes.

19. The diaper of claim 18 wherein the side margins comprise a pair of breathable leg cuffs between the forward and rearward portions which are each elasticized by a plurality of elastic threads, causing the side margins to become upstanding from the surface of the top sheet.

20. The diaper of claim 15 wherein the core contains a hydrogel.

21. The diaper of claim 20 wherein the core further comprises: a top fluid acquisition layer, situated between the end and side margins respectively, and having a fluid target zone; and a bottom fluid storage layer containing substantially all of the hydrogel.

22. The diaper of claim 21 wherein the bottom layer comprises a discrete pledget having a lesser surface area than the top layer.

23. The diaper of claim 22 wherein the pledget is positioned in the front portion of the chassis assembly.

* * * * *

UNITED STATES PATENT AND TRADEMARK OFFICE
CERTIFICATE OF CORRECTION

PATENT NO. : 5,135,522  
DATED : August 4, 1992  
INVENTOR(S) : Anne M. Fahrenkrug, et al It is certified that error appears in the above-indentified patent and that said Letters Patent is hereby corrected as shown below:

Abstract, Line 4, "liquid-previous" should read --liquid-pervious--

Column 4, line 66, "shown) Which," should read --shown) which--

Column 5, line 25, "is," should read --18,--

Column 6, line 24, "Varying" should read --varying--

Column 6, line 42, "core Is" should read --core 18--

Column 6, line 64, "FIG. 30" should read --FIG. 3C--

Column 7, line 41, "(FIGS. and 2)" should read --(FIGS. 1 and 2)--

Column 8, line 20, "shown, the" should read --shown in FIG. 2, the--

Column 9, line 8, "core Is" should read --core 18--

Column 9, line 46, "20," should read --20",--

UNITED STATES PATENT AND TRADEMARK OFFICE
CERTIFICATE OF CORRECTION

PATENT NO. : 5,135,522

DATED : August 4, 1992

INVENTOR(S) : Anne, M. Fahrenkrug, et al

It is certified that error appears in the above-indentified patent and that said Letters Patent is hereby corrected as shown below:

Column 10, line 48, "52 FIG." should read --52 (FIG.--

Signed and Sealed this

Fifth Day of October, 1993

Attest:

BRUCE LEHMAN

*Attesting Officer*      *Commissioner of Patents and Trademarks*